United States Patent [19]

Sattler et al.

[11] Patent Number: 4,902,682
[45] Date of Patent: Feb. 20, 1990

[54] W/O CREAM CONTAINING HYDROCORTISONE DIESTER

[75] Inventors: Henning Sattler, Hamburg; Bodo Asmussen, Ammersbek, both of Fed. Rep. of Germany

[73] Assignee: Beiersdorf AG, Hamburg, Fed. Rep. of Germany

[21] Appl. No.: 904,538

[22] Filed: Sep. 5, 1986

[30] Foreign Application Priority Data

Sep. 28, 1985 [DE] Fed. Rep. of Germany ....... 3534742

[51] Int. Cl.⁴ ............................................... A61K 47/00
[52] U.S. Cl. .................................................... 514/179
[58] Field of Search ......................... 514/179, 180-181

[56] References Cited

U.S. PATENT DOCUMENTS

| | | | |
|---|---|---|---|
| 4,252,796 | 2/1981 | Yu et al. | 514/181 |
| 4,284,630 | 8/1981 | Yu et al. | 514/180 |

FOREIGN PATENT DOCUMENTS

| | | |
|---|---|---|
| 098566 | 1/1984 | European Pat. Off. . |
| 131821 | 1/1985 | European Pat. Off. . |
| 2826257 | 12/1979 | Fed. Rep. of Germany . |
| 2851544 | 6/1980 | Fed. Rep. of Germany . |
| 3402877 | 3/1984 | Fed. Rep. of Germany . |
| 3402880 | 8/1984 | Fed. Rep. of Germany . |
| 2539991 | 8/1984 | France . |
| 2539992 | 8/1984 | France . |

OTHER PUBLICATIONS

Takashima, Chem. Abst. vol. 103, 220828m, 1985.

*Primary Examiner*—Mark L. Berch
*Attorney, Agent, or Firm*—Sprung Horn Kramer & Woods

[57] ABSTRACT

The invention relates to a cream containing hydrocortisone diester, which contains
0.01-0.5% of hydrocortisone diester,
1-10% of beeswax or beeswax substitute,
1-25% of liquid paraffin,
25-75% of white vaseline,
0-2% of aluminium stearate,
2-20% of W/O emulsifier based on straight-chain and branched hydrocarbons, glyceryl oleate and wool wax alcohols or polyglyceryl-4 isostearate and hydrogenated castor oil,
0-2% of hydrated magnesium sulphate and
10-60% of water.

7 Claims, No Drawings

W/O CREAM CONTAINING HYDROCORTISONE DIESTER

The present invention relates to a new cream which contains hydrocortisone diester.

An oily ointment or fatty ointment containing the active ingredient hydrocortisone 17-butyrate 21-propionate has already been disclosed in German Offenlegungsschrift 3,402,877.

Ointments whose water content is zero or only very low do not form emulsions, and thus are not creams. Formulations of this type are not always satisfactory in respect of absorption of active ingredient. Moreover, inconveniences are associated with their use.

Furthermore, an O/W cream containing the active ingredient hydrocortisone 17-butyrate 21-propionate is disclosed in German Offenlegungsschrift 3,402,880.

However, the cream base described has not always proved satisfactory, especially in respect of storage stability, that is to say the stability of the content of active ingredient. This particularly applies to the case where hydrocortisone diesters other than the diester described in this citation are used with the specified base.

The object of the invention is to provide a W/O cream which contains a hydrocortisone diester and which ensures satisfactory storage stability and high absorption of the active ingredient through the skin. The particular intention is to produce a W/O cream which contains hydrocortisone 17-propionate 21-acetate and has these properties.

This object is achieved by a W/O cream which is characterized in that it contains
- 0.01–0.5% of hydrocortisone diester,
- 1–10% of beeswax or beeswax substitute,
- 1–25% of liquid paraffin,
- 25–75% of white vaseline,
- 0–2% of aluminium stearate,
- 2–20% of W/O emulsifier based on straight-chain and branched hydrocarbons, glyceryl oleate and wool wax alcohols or polyglyceryl-4 isostearate and hydrogenated castor oil,
- 0–2% of hydrated magnesium sulphate and
- 10–60% of water.

The W/O cream preferably contains:
- 0.025–0.2% of hydrocortisone diester,
- 2–8% of beeswax or beeswax substitute,
- 5–15% of liquid paraffin,
- 40–60% of white vaseline,
- 0.2–1% of aluminium stearate,
- 5–15% of W/O emulsifier based on straight-chain and branched hydrocarbons, glyceryl oleate and wool wax alcohols or polyglyceryl-4 isostearate and hydrogenated castor oil,
- 0.5–1% of hydrated magnesium sulphate and
- 15–40% of water, but in particular:
- 0.13% of hydrocortisone diester
- 5% of beeswax or beeswax substitute
- 9% of liquid paraffin
- 50.5% of white vaseline
- 0.5% of aluminium stearate
- 10% of W/O emulsifier based on straight-chain and branched hydrocarbons, glyceryl oleate and wool wax alcohols or polyglyceryl-4 isostearate and hydrogenated castor oil
- 0.7% of hydrated magnesium sulphate and
- 24.17% of water.

All the stated amounts, proportions and percentages are based on weight.

Suitable hydrocortisone diesters are known and are specified in, for example, German Offenlegungsschriften 2,910,899 and 2,826,257. Preferred esters are
- hydrocortisone 17-propionate 21-acetate,
- hydrocortisone 17-butyrate 21-acetate,
- hydrocortisone 17,21-dipropionate,
- hydrocortisone 17-propionate 21-butyrate, and
- hydrocortisone 17-butyrate 21-propionate.

Very particularly preferred W/O cream formulations according to the invention are those containing hydrocortisone 17alpha-propionate 21-acetate as the main active ingredient.

They are distinguished by particularly high storage stability and high efficacy. Even after storage for several years there is virtually no measurable decrease in the content of active ingredient.

Preferred beeswax substituted are those based on partial glycerides and esters of long-chain fatty acids, which are marketed under the trade name "Cutina BW" (by Henkel).

The liquid paraffin which is preferably used is low-viscosity liquid paraffin.

The cream preferably contains aluminium stearate in the amount indicated.

Particularly preferred W/O emulsifiers are those based on a mixture of straight-chain and branched hydrocarbons, glyceryl oleate and wool wax alcohols or polyglyceryl-4 isostearate and hydrogenated castor oil, and whose hydrocarbon contribution is preferably formed by paraffin, vaseline and ozokerite.

Emulsifiers of this type are described in the literature (CTFA Cosmetic Ingredient Dictionary, 3rd edition, The Cosmetics, Toiletry and Fragrance Association, Inc. 1110 Vermont Avenue, N.W. Washington, D.C. 20005, in particular pages 505, 230, 196, 123, 111, 112 and 243) and are obtainable under the trade names Protegin, Protegin, W, Protegin WX and Protegin X (supplied by Goldschmidt, Germany). The types Protegin W and WX are preferred, but Protegin WX is particularly preferred and has proved to be particularly advantageous. Protegin and Protegin X contain wool wax alcohols, while Protegin W and Protegin WX contain polyglyceryl-4 isostearate and hydrogenated castor oil.

The hydrocarbon contribution to Protegin and Protegin X consists of paraffin, vaseline and ozokerite, and that of Protegin W and Protegin WX consists of vaseline and ozokerite.

The cream according to the invention preferably contains magnesium sulphate, and magnesium sulphate $.7H_2O$ is particularly used.

In addition, it is possible for smaller proportions of additives such as glycerol, propylene glycol, isopropyl fatty acid esters, such as isopropyl myristate and isopropyl palmitate, waxes, for example hydrocarbon waxes, such as ozokerite, and beeswax and spermaceti and their substitutes, as well as agents for controlling the pH and preservatives, although these are not generally necessary in the cream according to the invention, to be present.

The new cream according to the invention provides a W/O cream which contains a hydrocortisone diester, in particular hydrocortisone 17-propionate 21-acetate, and which is distinguished by high efficacy and high storage stability.

To prepare the cream, the constituents of the fatty phase such as vaseline, paraffin, beeswax or beeswax substitute, aluminium stearate and the emulsifier are melted and brought to 60° to 80° C. The magnesium sulphate is dissolved in water, the aqueous phase likewise being heated to 60°–80° C. The two phases are mixed and, at a temperature of about 60° C., the active ingredient hydrocortisone diester is added. The composition is stirred while it is allowed to cool and solidify.

The active ingredient is very efficiently absorbed from the cream according to the invention, which has an outstanding storage stability. It is used for the treatment of eczemas, dermatitis, psoriasis and inflammations.

To cure or treat these disorders, the cream according to the invention can be applied topically to the lesions. The amount of cream which is applied varies in accordance with the concentration of the active ingredient in the cream. In general, a suitable amount is applied to the lesion several times a day, depending on the severity of the disorder which is to be treated.

The examples which follow serve to illustrate the invention:

EXAMPLE 1

A W/O cream is prepared with the specified constituents:

| | |
|---|---|
| hydrocortisone 21-acetate 17-propionate | 0.127 g |
| W/O emulsifier based on straight-chain and branched hydrocarbons, glyceryl oleate and polyglyceryl-4 isostearate and hydrogenated castor oil (Protegin WX) | 10 g |
| beeswax substitute (Cutina BW) | 5 g |
| liquid paraffin | 9 g |
| white vaseline | 50.5 g |
| aluminium stearate | 0.5 g |
| magnesium sulphate | 0.7 g |
| purified water | 24.173 g |
| | 100.000 g |

The beeswax substitute, vaseline, paraffin, aluminium stearate and the emulsifier are heated to 75° C., and the magnesium sulphate and water are likewise heated to 75° C., with dissolution of the salt. The phases are mixed and, after cooling to 60° C., the hydrocortisone 17-propionate 21-acetate is added, and the composition is stirred until cold.

EXAMPLE 2

A W/O cream is prepared with the specified constituents:

| | |
|---|---|
| hydrocortisone 21-acetate 17-propionate | 0.050 g |
| W/O emulsifier based on straight-chain and branched hydrocarbons, glyceryl oleate and polyglyceryl-4 isostearate and hydrogenated castor oil (Protegin WX) | 5.0 g |
| beeswax substitute (Cutina BW) | 6.0 g |
| liquid paraffin | 15.0 g |
| white vaseline | 50.0 g |
| purified water | 23.95 g |
| | 100.000 g |

The beeswax substitute, vaseline, paraffin and the emulsifier are heated to 75° C. The water is likewise heated to 75° C., with dissolution of the salt. The phases are mixed and, after cooling to 60° C., the hydrocortisone 17-propionate 21-acetate is added, and the composition is stirred until cold.

EXAMPLE 3

A W/O cream is prepared with the specified constituents:

| | |
|---|---|
| hydrocortisone 21-acetate 17-propionate | 0.100 g |
| W/O emulsifier based on straight-chain and branched hydrocarbons, glyceryl oleate and polyglyceryl-4 isostearate and hydrogenated castor oil (Protegin W) | 15.0 g |
| beeswax substitute (Cutina BW) | 5.0 g |
| liquid paraffin | 14.0 g |
| white vaseline | 41.0 g |
| magnesium sulphate | 0.5 g |
| purified water | 24.4 g |
| | 100.000 g |

The beeswax substitute, vaseline, paraffin and the emulsifier are heated to 75° C. The magnesium sulphate and water are likewise heated to 75° C., with dissolution of the salt. The phases are mixed and, after cooling to 60° C., the hydrocortisone 17-propionate 21-acetate is added, and the composition is stirred until cold.

EXAMPLE 4

A W/O cream is prepared with the specified constituents:

| | |
|---|---|
| hydrocortisone 17-butyrate 21-acetate | 0.127 g |
| W/O emulsifier based on straight-chain and branched hydrocarbons, glyceryl oleate and wool wax alcohols (Protegin X) | 10 g |
| beeswax substitute (Cutina BW) | 5 g |
| Liquid paraffin | 9 g |
| white vaseline | 50.5 g |
| aluminium stearate | 0.5 g |
| magnesium sulphate | 0.700 g |
| purified water | 24.173 g |
| | 100.000 g |

The beeswax substitute, vaseline, paraffin, aluminium stearate and the emulsifier are heated to 75° C. The magnesium sulphate and water are likewise heated to 75° C., with dissolution of the salt. The phases are mixed and, after cooling to 60° C., the hydrocortisone 17-butyrate 21-acetate is added, and the composition is stirred until cold.

EXAMPLE 5

A W/O cream is prepared with the specified constituents:

| | |
|---|---|
| hydrocortisone 17-butyrate 21-propionate | 0.127 g |
| W/O emulsifier based on straight-chain and branched hydrocarbons, glyceryl oleate and polyglyceryl-4 isostearate and hydrogenated castor oil (Protegin WX) | 10 g |
| beeswax substitute (Cutina BW) | 5 g |
| liquid paraffin | 9 g |
| white vaseline | 50.5 g |
| aluminium stearate | 0.5 g |
| magnesium sulphate | 0.700 g |
| purified water | 24.173 g |
| | 100.000 g |

The beeswax substitute, vaseline, paraffin, aluminium stearate and the emulsifier are heated to 75° C. The magnesium sulphate and water are likewise heated to 75° C., with dissolution of the salt. The phases are mixed and, after cooling to 60° C., the hydrocortisone 17-butyrate 21-propionate is added, and the composition is stirred until cold.

I claim:

1. A water-in oil cream containing hydrocortisone diester, characterized in that it contains
   0.01–0.5% of hydrocortisone diester,
   1–10% of beeswax or beeswax substitute,
   1–25% of liquid paraffin,
   25–75% of white vaseline,
   0–2% of aluminium stearate,
   2–20% of W/O emulsifier based on straight-chain and branched hydrocarbons, glyceryl oleate and wool wax alcohols or polyglyceryl-4 isostearate and hydrogenated castor oil,
   0–2% of hydrated magnesium sulphate and
   10–60% of water.

2. A water-in-oil cream according to claim 1, characterized in that it contains hydrocortisone 17-propionate 21-acetate.

3. A water-in-oil cream according to claim 1, characterized in that it contains hydrocortisone 17-butyrate 21-acetate.

4. A water-in-oil cream according to claim 1, characterized in that it contains hydrocortisone 17-butyrate 21-propionate.

5. A water-in-oil cream according to claim 1, characterized in that it contains
   0.13% of hydrocortisone 17-propionate 21-acetate,
   5% of beeswax or beeswax substitute,
   9% of liquid paraffin,
   50.5% of white vaseline,
   0.5% of aluminium stearate,
   10% of W/O emulsifier based on straight-chain and branched hydrocarbons, glyceryl oleate and wool wax alcohols or polyglyceryl-4 isostearate and hydrogenated castor oil
   0.7% of hydrated magnesium sulphate and
   24.17% of water.

6. A method of treating a patient afflicted with a skin inflammation, psoriasis or eczema which comprises applying to such patient's skin an amount effective therefor of a cream according to claim 1.

7. Process for the preparation of the water-in-oil cream according to claim 1, characterized in that
   1–10% of beeswax or beeswax substitute,
   1–25% of liquid paraffin,
   25–75% of white vaseline,
   0–2% of aluminium stearate,
   2–20% of W/O emulsifier based on straight-chain and branched hydrocarbons, glyceryl oleate and wool wax alcohols or polyglyceryl-4 isostearate and hydrogenated castor oil are brought to 60°–80° C. and mixed with
   0–2% of hydrated magnesium sulphate dissolved in
   10–60% of water at 60°–80° C., and, at about 60° C.,
   0.01–0.5% of hydrocortisone diester is added, and the composition is allowed to solidify while Stirring.

* * * * *